(12) United States Patent
Li et al.

(10) Patent No.: US 11,451,522 B2
(45) Date of Patent: Sep. 20, 2022

(54) SYSTEM AND METHOD FOR ENABLING THE SECURE STORAGE, TRANSMISSION AND ACCESS OF GENETIC DATA

(71) Applicant: City University of Hong Kong, Kowloon (HK)

(72) Inventors: Shuai Cheng Li, Kowloon (HK); Wei Dong, Kowloon (HK)

(73) Assignee: City University of Hong Kong, Kowloon (HK)

( * ) Notice: Subject to any disclaimer, the term of this patent is extended or adjusted under 35 U.S.C. 154(b) by 257 days.

(21) Appl. No.: 16/002,136

(22) Filed: Jun. 7, 2018

(65) Prior Publication Data

US 2019/0379647 A1 Dec. 12, 2019

(51) Int. Cl.
*H04L 29/06* (2006.01)
*H04L 9/40* (2022.01)
*G16H 10/60* (2018.01)
*G16B 50/00* (2019.01)

(52) U.S. Cl.
CPC .......... *H04L 63/0464* (2013.01); *G16B 50/00* (2019.02); *G16H 10/60* (2018.01)

(58) Field of Classification Search
CPC ............. H04L 63/0464; H04L 63/1466; H04L 2463/121; H04L 63/0478; G16H 10/60; G16H 10/40; G06F 21/6245; G16B 50/40
See application file for complete search history.

(56) References Cited

U.S. PATENT DOCUMENTS

| | | | |
|---|---|---|---|
| 10,515,567 B2 * | 12/2019 | Lablans | G06F 7/4876 |
| 2009/0282256 A1 * | 11/2009 | Rakic | H04L 63/12 |
| | | | 713/176 |
| 2016/0224735 A1 * | 8/2016 | Ayday | G16H 10/60 |
| 2018/0218114 A1 * | 8/2018 | Wesselman | G06F 16/13 |
| 2018/0330052 A1 * | 11/2018 | Barrus | G16B 50/40 |

* cited by examiner

*Primary Examiner* — Fatoumata Traore
*Assistant Examiner* — Carlton Johnson
(74) *Attorney, Agent, or Firm* — Renner Kenner Greive Bobak Taylor & Weber (57) ABSTRACT

A system and method for a computer system for the secure storage, transmittance and access of genetic data includes a coordinator server including a coordinator program arranged to update secure access information, the coordinator server being in communication with a genetic data sequencing server, a genetic data analysing server, and a genetic data storage server, whereby the coordinator server communicates the secure access information in a manner to allow the genetic data storage server to act as a proxy server between the genetic data sequencing server and the genetic data analysing server.

41 Claims, 7 Drawing Sheets

SYSTEM AND METHOD FOR ENABLING THE SECURE STORAGE, TRANSMISSION AND ACCESS OF GENETIC DATA

TECHNICAL FIELD

The present invention relates to a system and method for ensuring the safe storage, transmission and access of an individual's genetic data. In one specific embodiment, the invention provides a decentralised data network which uses multiple layers of cryptographic protection and identity authentication. The high level of protection the present invention provides enables an individual's genetic data to be only accessed by that individual's computer server, or other computer servers that have been granted conditional access to the data by the individual to whom the genetic data relates.

BACKGROUND

In the past, medical records were often physical documents, which were directly shared between specific medical practitioners, or between a medical practitioner and their patient. However, with the ubiquitous use of digital data storage and digital communication, there is an increasing need for any personal medical data or information to be available to the owner of the medical data or information or be accessed by specific authorised medical practitioners at anytime and anywhere in the world. Much like any form of medical data or information, genetic data can be sensitive, and the individuals to which the information belongs may be adversely affected by the leakage of such data.

The leakage of an individual's genetic data can lead to serious problems. Firstly, models are available that use genetic data to reconstruct a three-dimensional facial structure of the owner from the genetic data, which would compromise any security system that utilises facial recognition as a biometric authentication method. Further, genetic and medical data relate to very sensitive issues for the owner of the genetic data or their relatives. The leakage of knowledge relating to an ancestor, a susceptibility to certain diseases, or presence of carrier genes is highly personal information that may be used surreptitiously by other parties.

Therefore, it is common for genetic data to be anonymised, that is, the data is modified to remove any attributes that may associate it with the owner of the genetic data. However, increasingly there are examples where de-anonymising methods have been used to identify the owner of the data using a variety of other sources. For example, one of the approaches is to collect images from social media and extract facial traits and match these traits against anonymous genetic data. With online social networking and other technologies playing increasingly important roles in our lives, it is likely that the de-anonymizing methods will continue to improve in accuracy, which will greatly decrease the security of anonymising medical data.

Further, Governments have enacted legislative instruments in support of ensuring genetic data is protected by ensuring that organisations providing the service of securing and transmitting genetic data have sufficient levels of protection in place. Such protection would rely on the use of a reliable centralized database which includes numerous limitations and requirements for service providers, such as only using restricted genetic sequences and the requirement to publish their prediction algorithms before requesting access to the genetic data.

Further legislative instruments have been implemented and to ensure appropriate punishment for those who violate the privacy of the public. However, there is little relief for the victims of such violations, as once data has been leaked, it is nearly impossible to recapture the data.

Accordingly, it would be useful to provide a solution that preferably avoids or ameliorates any one or more of the disadvantages present in the current approaches to the storage and access of genetic data.

SUMMARY OF THE INVENTION

According to a first aspect of the invention, there is provided a computer system for the secure storage, transmittance and access of genetic data comprising: a coordinator server including a coordinator program arranged to update secure access information, the coordinator server being in communication with a genetic data sequencing server, a genetic data analysing server, and a genetic data storage server.

Preferably, the coordinate server does not participate in activities related to storage, transmittance and access of genetic data.

The coordinator server may communicates the secure access information in a manner which allow the genetic data storage server to act as a proxy server between the genetic data sequencing server and the genetic data analysing server.

The coordinator server, the genetic data storage server, the genetic data generating server, and the genetic data analysing server communicate though the exchange of one or more signatures.

The genetic data generating server encrypts the genetic data using an encryption key created by the data owner server.

The genetic data generating server transmits the encrypted data to the genetic data storage server.

The genetic data storage server is instructed to re-encrypt the encrypted genetic data using a re-encryption key created by the data owner server.

The genetic data storage server transmits the re-encrypted data to the genetic data analysing server.

The coordinator program instructs the genetic data analysing server to delete the genetic data after the genetic data is analysed.

According to a second aspect of the invention, there is provided a computing network for the secure storage, transmittance and access of genetic data comprising: a genetic data generating server which is in communication with a genetic data storage server, where the genetic data storage server is in communication with a genetic data analysing server, wherein the genetic data is encrypted by the genetic data generating server and decrypted by the genetic data analysing server.

The genetic data may also be encrypted by the genetic data storage server.

The coordinator server, the genetic data storage server, the genetic data generating server, and the genetic data analysing server are in secure communication though the exchange of one or more signatures.

The data owner generates a decryption key using a cryptographic operation.

The cryptographic operation includes a series of one or more previous cryptographic operations.

The series of one or more previous cryptographic operations are encrypted by a hash function.

The decryption key is used to generate an encryption key by means of elliptic curve cryptography.

The genetic data generating server encrypts the genetic data using the encryption key created by the data owner server. The encryption key may be created when the sequence is generated.

The genetic data generating server transmits the encrypted data to the genetic data storage server.

The genetic data storage server is instructed to re-encrypt the encrypted genetic data using a re-encryption key created by the data owner server.

The genetic data storage server transmits the re-encrypted data to the genetic data analysing server.

The installed coordinator program instructs the genetic data analysing server to delete the genetic data after the genetic data is analysed.

According to a third aspect of the invention, there is provided a computer system for the secure storage, transmittance and access of genetic data comprising: a coordinator server including secure access data and in communication with a data owner server, a genetic data storage server, a genetic data generating server, and a genetic data analysing server, wherein the genetic data storage server stores the encrypted genetic data transmitted from the genetic data generating server and re-encrypts the encrypted data prior to transmission of the encrypted genetic data to the genetic data analysing server whereby the genetic data analysing server can only unencrypt the genetic data upon receipt of the secure access information from the coordinator.

The coordinator server, the genetic data storage server, the genetic data generating server, and the genetic data analysing server are in secure communication though the exchange of one or more signatures.

The data owner generates a decryption key using a cryptographic operation.

The cryptographic operation includes a series of one or more previous cryptographic operations.

The series of one or more previous cryptographic operations are encrypted by a hash function.

The decryption key is used to generate an encryption key by means of elliptic curve cryptography.

The secure accessing information includes at least one or time stamp data and the encryption key.

The genetic data analysing server receives further secure access information from the owner to unencrypt the information.

According to a fourth aspect of the invention, there is provided a computer enabled method for the secure storage, transmittance and access of genetic data comprising: a coordinator in communication with a data owner server, a genetic data storage server, a genetic data generating server, and a genetic data analysing server, whereby the coordinator server operates as a proxy server in a decentralised data sharing network by verifying the identity of each of the genetic data storage server, the genetic data generating server, and the genetic data analysing server and facilitates the secure transmittance and storage of the genetic data by updating the central collection of asymmetric public encryption keys that are generated by the data owner server, the genetic data storage server, the genetic data generating server, and the genetic data analysing server.

These encryption keys may be used to generate secure communication between various servers.

The coordinator server verifies the identities of the data owner server, the genetic data storage server, the genetic data generating server, and the genetic data analysing server.

The data owner generates a decryption key using a cryptographic operation.

The cryptographic operation includes a series of one or more previous cryptographic operations.

The series of one or more previous cryptographic operations are encrypted by a hash function.

The decryption key is used to generate an encryption key by means of elliptic curve cryptography.

The coordinator server, the genetic data storage server, the genetic data generating server, and the genetic data analysing server securely communicate though the exchange of one or more signatures.

The genetic data generating server is instructed to encrypt the genetic data using an encryption key created by the data owner server.

The genetic data generating server is instructed to transmit the encrypted data to the genetic data storage server.

The coordinator program instructs the genetic data generating server to delete the genetic data after the genetic data is generated.

The genetic data storage server is instructed to re-encrypt the encrypted genetic data using a re-encryption key created by the data owner server.

The genetic data storage server transmits the re-encrypted data to the genetic data analysing server.

The coordinator program instructs the genetic data analysing server to delete the genetic data after the genetic data is analysed.

The genetic data storage server comprises of two or more genetic data storage servers.

The genetic data storage server may communicate with other genetic data storage servers.

The genetic data storage server is instructed to re-encrypt the encrypted genetic data using a re-encryption key created by the data owner server.

A first data storage server transmitting the re-encrypted genetic data to a second genetic data storage server designated by the data owner server.

The coordinator program instructs the first genetic data storage server to delete the encrypted genetic data after the second genetic data storage server has received the re-encrypted genetic data.

BRIEF DESCRIPTION OF THE DRAWINGS

Further features of the present invention are more fully described in the following description of several non-limiting embodiments thereof. This description is included solely for the purpose of exemplifying the present invention. It should not be understood as a restriction on the broad summary, disclosure or description of the invention as set out above. The description will be made with reference to the accompanying drawings in which.

DETAILED DESCRIPTION

Broadly, one of the inventive aspects is directed to a computer enabled method for the storage, transmittance and access of genetic data. In an embodiment, the invention is directed to a computer system for the secure storage, transmittance and access of genetic data comprising: a coordinator server including a coordinator program arranged to update secure access information, the coordinator server being in communication with a genetic data sequencing server, a genetic data analysing server, and a genetic data storage server, whereby the coordinator server communicates the secure access information in a manner to allow the genetic data storage server to act as a proxy server between the genetic data sequencing server and the genetic data analysing server.

Preferably, the coordinate server does not participate in activities related to storage, transmittance and access of genetic data.

In another aspect, the invention is directed to a computing network for the secure storage, transmittance and access of genetic data comprising: a genetic data generating server which is in communication with a genetic data storage server, where the genetic data storage server is in communication with a genetic data analysing server, wherein the genetic data is encrypted by the genetic data generating server and decrypted by the genetic data analysing server. Alternatively or additionally, the genetic data may also be encrypted by the genetic data storage server.

In another aspect, the invention is directed to a computer system for the secure storage, transmittance and access of genetic data comprising: a coordinator server including secure access data and in communication with a data owner server, a genetic data storage server, a genetic data generating server, and a genetic data analysing server, wherein the genetic data storage server stores the encrypted genetic data transmitted from the genetic data generating server and re-encrypts the encrypted data prior to transmission of the encrypted genetic data to the genetic data analysing server whereby the genetic data analysing server can only unencrypt the genetic data upon receipt of the secure access information from the coordinator.

In another aspect, the invention is directed to a computer system for the secure storage, transmittance and access of genetic data comprising: a coordinator, a data owner server, at least one genetic data storage server, at least one genetic data generating server, at least one genetic data analysing server, wherein the genetic data storage server stores the encrypted genetic data transmitted from the at least one genetic data generating server and re-encrypts the encrypted data prior to transmission of the encrypted genetic data to at least one of the at least one genetic data analysing server and another of the at least one genetic data storage server and such that the data centre server has no access to an unencrypted form of the encrypted genetic data.

In another aspect, the invention is directed to a computer enabled method for the secure storage, transmittance and access of genetic data comprising: a coordinator in communication with a data owner server, a genetic data storage server, a genetic data generating server, and a genetic data analysing server, whereby the coordinator server operates as a proxy server in a decentralised data sharing network by verifying the identity of each of the genetic data storage server, the genetic data generating server, and the genetic data analysing server and facilitates the secure transmittance and storage of the genetic data by updating the central collection of asymmetric public encryption keys that are generated by the data owner server, the genetic data storage server, the genetic data generating server, and the genetic data analysing server. These encryption keys may be used to generate secure communication between various servers.

Figure 1:
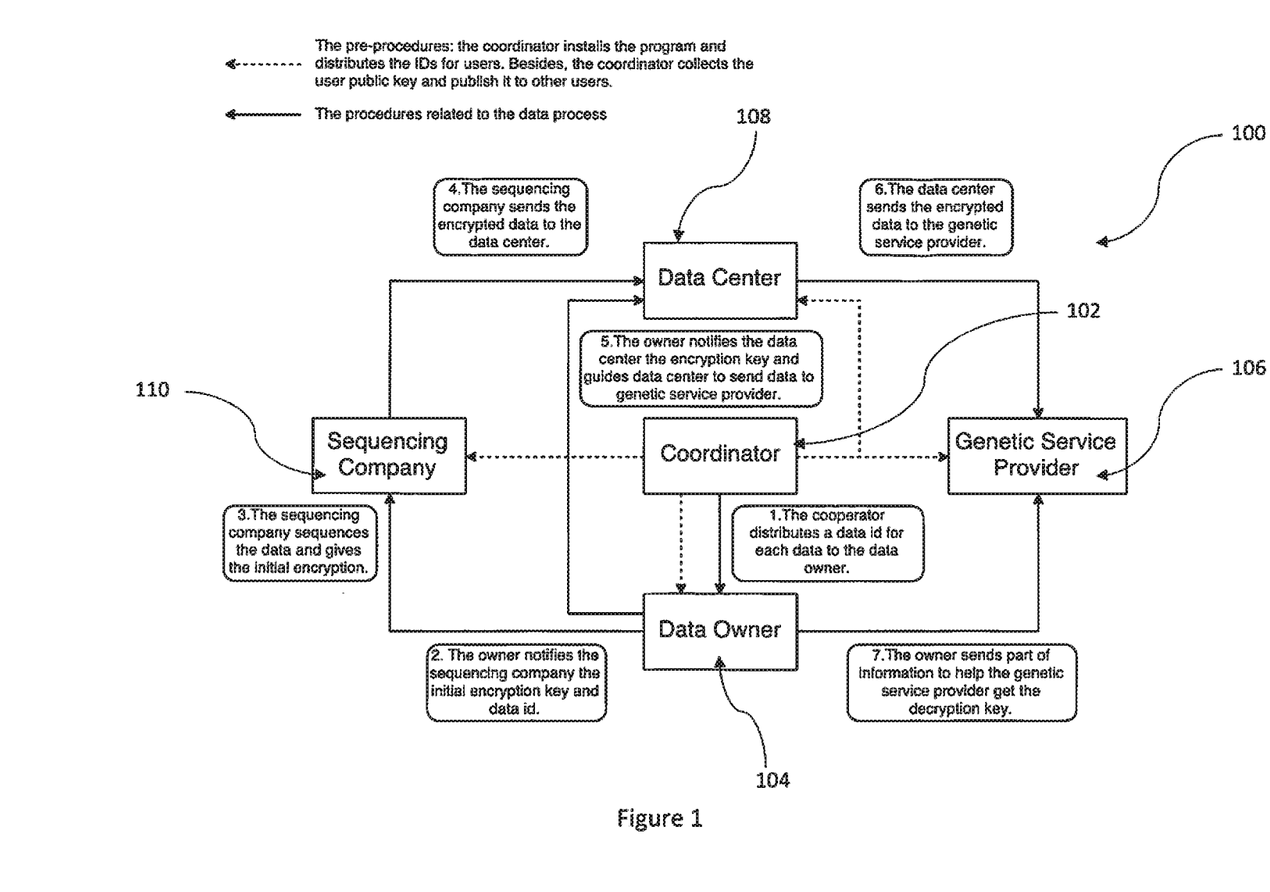
FIG. 1 shows an embodiment of present invention.

Specific embodiments will now be described in more detail with reference to the drawings. Referring to FIG. 1, the computer enabled system for the storage and access of genetic data 100. The system provides an interface and portal through which each type of server may access, store, transmit, or use genetic data. There are five types of servers; a coordinator server, a data owner server, a genetic data analysing server, a data storage server and a genetic data generating server.

In more detail, the present invention includes a coordinator program 102 installed on a coordinator server, which updates secure access information data. In the context of the present invention, the term "secure access information" is used to refer to the data used to encrypt or decrypt the data owner's genetic data. The secure access information may refer to data used to ensure secure communication between servers and/or a part of data used to encrypt or decrypt the data owner's genetic data.

Secure access information may include public key cryptographic information and time stamp data. The coordinator also performs the task of continuously updating and making available for use the secure access information. The coordinator may also install programs and assign unique identifying numbers (ID) to each of the other servers and to the data owner server's genetic data.

The coordinator 102 may also evaluate the various genetic analysing, storage and generating servers, and keep data owner servers informed of the risks of using the system. In an alternate embodiment, the coordinator 102 is a program that semi or fully autonomously undertakes the above tasks and communicates with each of the servers.

A data owner is the person from which the genetic data was collected. Accordingly, a data owner server, is the server accessible by and under the control of the data owner. In an embodiment, the data owner server 104 manages the operations related to the data owner's genetic data. The operations may include delegating which genetic data sequencing, storage, or analysing server to communicate with, authorising the transmission of genetic data, supplying the coordinator program 102 with new public cryptographic information stored on the system, and authorising any access to the genetic data.

In an embodiment, the cryptographic information for encrypting and decrypting of the genetic data is created locally by a program installed on the data owner server 104, and this cryptographic creation is only performed on the data owner server 104. In an embodiment, the cryptographic information includes an asymmetric cryptographic key pair of an encryption key and a decryption key, which are generated by a program on the data owner server 104. Such asymmetric cryptographic systems are highly effective at protecting the security of data. An example of an early asymmetric cryptographic system is Pretty Good Privacy (PGP) (https://www.openpgp.org/). The example is merely provided to assist the reader in understanding the workings of the embodiments and the broader invention described and defined herein. It will be understood that a person skilled in the art will understand the use of such system as an integer of the embodiments and broader invention described and defined herein.

The genetic data analysing server 106 analyses the genetic data and provides genetic services for the data owner server 104. The genetic data analysing server 106 may also be referred to as a genetic data analysing server. After receiving the genetic data from a data centre server 108, the genetic data analysing server 106 decrypts the genetic data as instructed by the data owner server 104.

The data centre 108 provides storage services for the genetic data to the data owner servers 104. In an embodiment, the data centre server 108 provides further encryption services through proxy re-encryption technology by encrypting the data with an encryption key provided by data owner server 104. The unencrypted or raw genetic data is not available to the data centre server 108. In an embodiment, the data centre server 108 is also responsible for transmitting the encrypted genetic data to the genetic data analysing 106 according to the requirement of the data owner server 104. The data centre server 108 may also be referred to as a genetic data storage server.

A genetic data generating server 110 obtains raw genetic data from a sample provided by the data owner and sequences the sample using conventional methods. Accordingly, the genetic data generating server is also referred to as the genetic data sequencing server. The genetic data sequencing server 110 encrypts the data owner's raw genetic data by means of an encryption key provided by the data owner server 104. Once the data owner server 104 issues instructions to transmit the data, the genetic data sequencing server 110 forwards the encrypted genetic data to the data centre 108. In an embodiment, the encryption process is integrated into the sequencing procedure, such that the encryption of the genetic data occurs alongside the sequencing procedure resulting in the genetic sequence being outputted in an encrypted format.

The computer enabled system 100 provides a decentralised network that segregates communication between certain servers and prevents certain servers from accesses to the raw genetic data. In doing so, the computer enabled system 100 protects the genetic data by breaking the process into multiple sub-procedures that are carried out by different combinations of servers. In an embodiment, the computer system 100 performs five sub-procedures, namely pre-process, data storage, data movement, data re-encryption and data process. For each sub-procedure, the data owner server 104 will authorise one or more servers to undertake one or more sub-procedures in order to enable secure access, transmit or storage of the genetic data. A number of different systems are included in the sub-procedures to ensure the security of the genetic data. Each of the sub-procedures are described in further detail in a later section. However, firstly the asymmetric cryptography system and signature system are described below.

Asymmetric Cryptography System

In an embodiment, an asymmetric cryptography system is used to encrypt the data to prevent the data from being read by anyone that does not possess the decryption key to decrypt the data. An asymmetric cryptography system is a cryptography system that uses two different keys; a private key and a public key. The keys are generated through the use of cryptographic algorithms. The public key is used to encrypt data into cyphertext and is made available to anyone. The private key is only known to the recipient of the encrypted data, where on receipt, the recipient uses their private key to decrypt the data into readable plaintext. Accordingly, the embodiment including the asymmetric cryptography system generates a decryption key, and related encryption key, where only the data owner server and servers authorised by the data owner server can access decryption key to decrypt the encrypted genetic data.

In an embodiment, the asymmetric cryptography system includes a chain of cryptographic key tables. The cryptographic key table includes of a number of different data, being the Genetic Data, Server, and Data owner identification (ID), the time stamp, the key for the table and the hash result of the previous cryptographic key table. Only the data owner server possesses all the information required to complete the cryptographic key table as it is created locally in a program on the data owner server and is only available to the data owner. An authorised server, such as the genetic data analysing server 106, can partially complete the table with the instructions of the coordinator and the data owner server. An example of a cryptographic key table is shown in table 1 as follows:

TABLE 1

| Cryptographic key table | |
|---|---|
| Genetic Data ID | Data owner server ID |
| Server ID | Time Stamp |
| The Key for the Table | |
| The Hash Result of the Last Table | |

To complete the cryptographic key table, the authorised server requires both the data ID but also IDs of the sender and the receiver, all of which are assigned by the coordinator. In an embodiment, cryptographic key table includes a time stamp, where the cryptography system considers time as being quantified into a series of blocks. For example, a block may include a time period of one week. However, as within the purview of the skilled addressee, any discrete time period could be quantified in this manner.

In an embodiment, further security is provided by the encryption of the time block by the coordinator. As the time block may be read by a server, it is susceptible to being completed by brute force guesswork, the encryption of the time block into time stamps through cryptographic algorithms. The cryptographic algorithms transform the time stamps into time blocks, examples of which are provided in Table 2 below.

TABLE 2

| Time block and time stamp | | |
|---|---|---|
| Time (y/m/d/h/m) | Time Block | Time Stamp |
| 2017/08/03/13/32 | 20170803 | E932 . . . |
| 2017/08/05/02/56 | 20170810 | 88JI . . . |
| 2017/08/09/07/17 | 20170810 | 88JI . . . |
| 2017/08/20/20/35 | 20170824 | 0I9I . . . |
| 2017/08/21/14/02 | 20170824 | 0I9I . . . |

When the cryptographic key table is created by the data owner server, the data owner server first is required to clarify who is allowed to access the data. Then, a time block is selected, during which the designated server is allowed to decrypt the data. Accordingly, the selected time block must be a future block in order to allow the recipient to receive the message. The data owner server will request the related time stamp from the coordinator and include the time stamp in the table.

Once the decrypted data has been provided to the authorised recipient, the receipt will wish to decrypt the genetic data. By way of a non-limiting example, the process is described in further detail.

When the genetic data analysing server attempts to complete the table to decrypt the data at a later stage, the genetic data analysing server ID that was assigned by the coordinator will be automatically added to the table by the cryptographic key system, wherein only the genetic data analysing server designated by the data owner server is able to decrypt the data.

The genetic data analysing server will then proceed to request the current time stamp from the coordinator. The structure of cryptographic key table and the time stamp data makes completing the cryptographic key table difficult for someone attempting to breach the system (an attacker), as it is very difficult for the attacker to obtain the required information to complete the table in order to decrypt the genetic data.

By way of an example, the difficulty overcoming the cryptographic system that is faced by an attacker is described in further detail. The example is provided merely to provide the reader with an understanding of the workings of the invention, and as such the reader would understand that no gloss is to be drawn from the example.

Firstly, the attacker would first have to guess the genetic data ID and the ID of the related data owner server. Secondly, an attacker would need to modify the cryptographic key system to allow them to input the genetic data analysing server ID manually. The cryptographic key table is represented in binary format. Therefore, the modification to the cryptographic key table required would be extremely difficult, if not impossible for the attacker to achieve. Even if the attacker was to succeed at modifying the cryptography system to enable the genetic data analysing ID to be entered, the attacker is still required to request and input the time stamp data within the correct time period allocated by the data owner server. Due to the size and complexity of the data required to decrypt the genetic data, it is nearly impossible for an attacker to guess or use a brute force attack to determine the required information.

Figure 2:
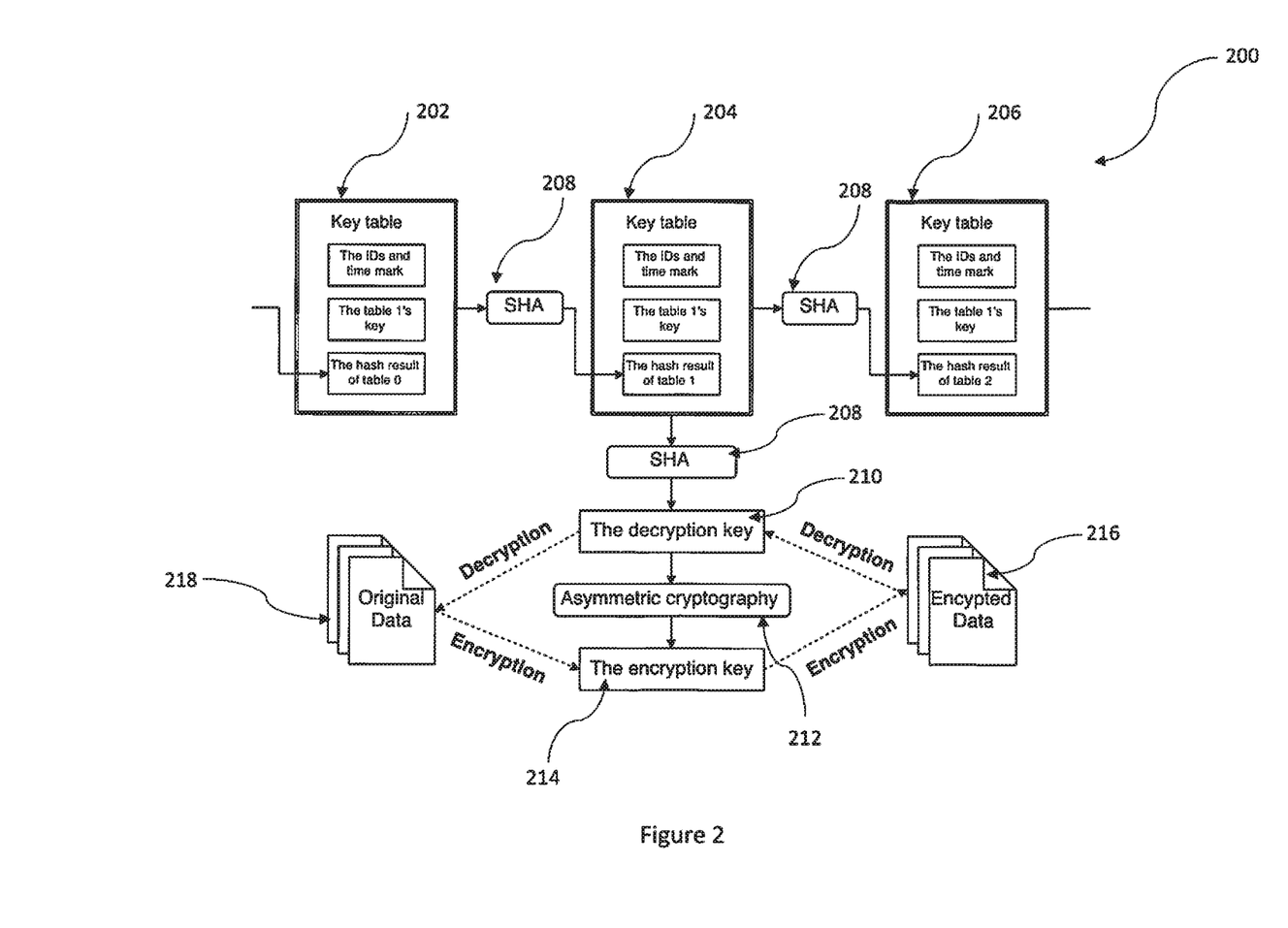
FIG. 2 shows an embodiment of the present invention.

Referring to FIG. 2, the cryptographic key system 200 is shown, which includes multiple cryptographic key tables 202, 204 and 206. When a server attempts to decrypt the data, the server will request the key first. This process ensures that any access to the data owner server's genetic data is undertaken only with the authority of the data owner server.

The content of the cryptographic key table is encrypted into a fixed-length string using a cryptographic hash function. A cryptographic hash function is a mathematical algorithm that maps data of any size into a string of bits of a fixed length and is designed to be infeasible to invert. In an embodiment, the cryptographic hash function may be one of the family of Secure Hash Algorithm functions such as, but not limited to, SHA-1, SHA-2, or SHA-3.

In an embodiment, the data owner server generates a new cryptographic key table each time the genetic data is encrypted or re-encrypted. Each new cryptographic key table that is generated includes the hashed results of the previous cryptographic key table. Linking newer tables to their predecessors in a chain, enables the entire life cycle of the key tables to be retained and provide a means through which the entire history of the cryptographic key tables can be determined. Furthermore, the linking of the cryptographic key tables improves the security of the cryptographic key system as extensive knowledge of the history of the data is required to decrypt the key tables, and therefore would be very unlikely to be determined without the information being provided by the data owner server. As such, each of the tables 202, 204 and 206 are generated by the data owner server, where each table includes the hash result of the preceding table. That is, table 204 includes the hash result of table 202 and table 206 includes the hash result of table 204.

In an embodiment, the content of the cryptographic key tables is run through a secure hash algorithm 208, such as SHA-3, to produce a decryption key 210. The encryption key 214 is obtained by running the decryption key through an asymmetric cryptography algorithm 212.

In an embodiment of the invention, the asymmetric cryptography algorithm 212 may include the use of elliptic curve cryptography. In particular, the elliptic curve cryptography algorithm relies on the algebraic structure of elliptic curves over finite fields. This elliptic curve cryptography algorithm relies on the inability to compute the multiplicand given the original and product points of the elliptic curve, especially when the size of the elliptic curve is very large. As would be understood by the skilled addressee, other curved cryptography algorithms may be used to determine the encryption key. Such alternative curve representations may include Hessian curves, Edwards curves or Twisted curves or other variations within the purview of the person skilled in the art.

The original data 218 is be encrypted by means of the encryption key 214. The decryption key 210 may be used to create the encryption key 214. As discussed above, the nature of the cryptography algorithm provides that inverting the encryption process to determine the decryption key 210 is virtually impossible. Therefore, the encrypted data 216 that has been encrypted by the encryption key 214 can only be decrypted with the decryption key 210.

Signature System

As described above, information is exchanged between servers through the computer system. Accordingly, the server sending the message is the sender and the server receiving the message is the recipient. In an embodiment, the information is shared through messages which include a digital signature to verify the authenticity of the messages.

The digital signature provides the identification, authentication, and secure data transfer between servers of the system. The digital signature system may include a number of security features, such as but not limited to; the server who is sending a message being the only person capable of using their digital signature, the server receiving the message being the only server capable of understanding the contents of the message, the provision of the signature for a single use, and the inclusion of a time cost for both signing and reading the signature is provided to prevent the occurrence of a random attack on the network.

Figure 3:
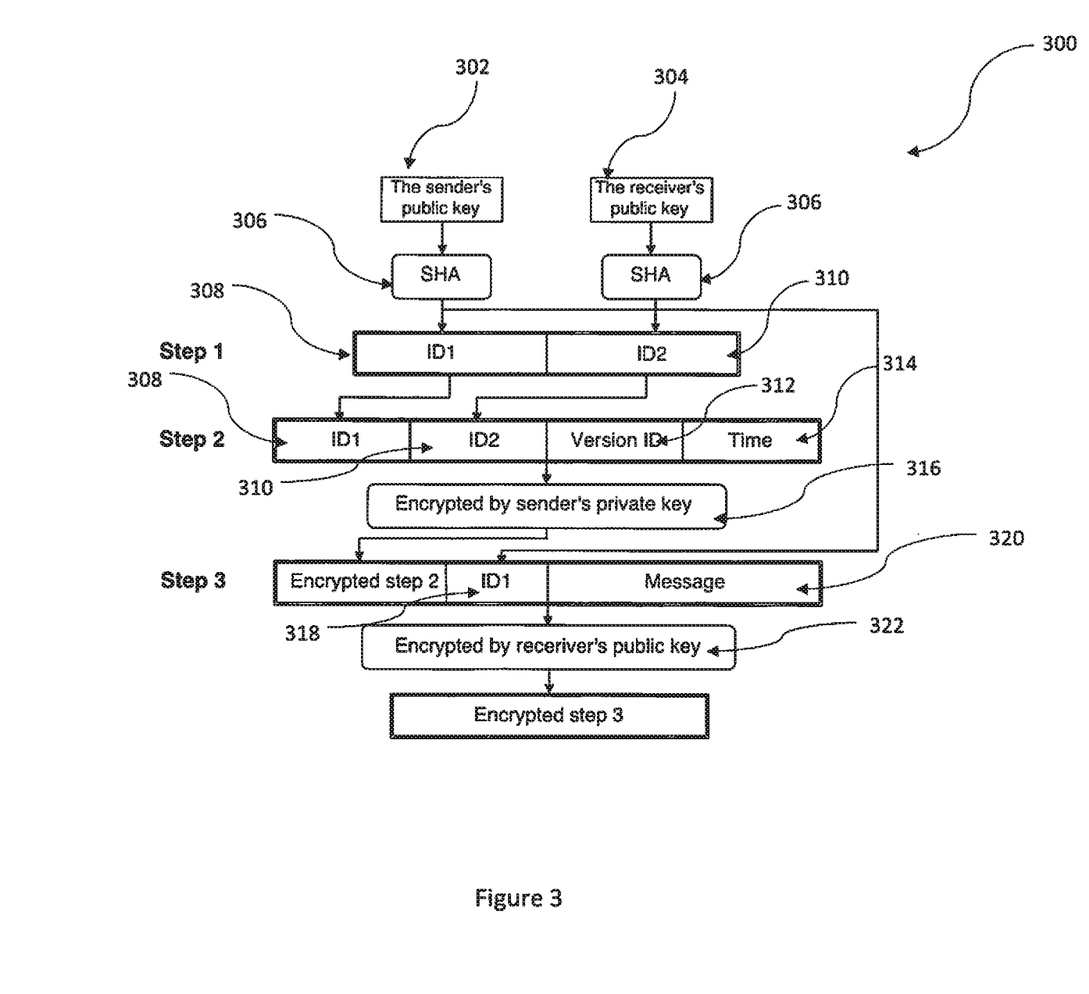
FIG. 3 shows an embodiment of the present invention.

An embodiment of the present invention includes the process for the creation of a digital signature 300 as shown in FIG. 3.

Firstly, the public key for the communication sender 302 and the public key for the communication receiver 304 are encrypted by means of a secure hash algorithm 306. This may include one of the algorithms of SHA-1, SHA-2, or SHA-3 or another corresponding hash function. Each of the hashed public keys are transferred into related IDs, being $ID_1$ 308 and $ID_2$ 310. Then, a version ID 312 is added to the signature to illuminate the purpose of the message to which the signature relates. For example. Whether the signature relates to the identification of a server, the provision of data ID, or a data transmission or transfer between servers. The signature further includes a time mark 314 which indicates the number of times the sender has been in previous communication with the recipient.

The signature content is initially encrypted by the sender's private key 316. The encrypted signature is then combined with the sender's ID 318 and a message 320 to be communicated to the recipient. For example, a message may include instructions from a data owner server to a first data centre server to transfer the genetic data to second data centre server. Or the message may include confirmation to the data owner server that the data has been transferred to a genetic service server. Once the message has been included, the entire signature and related message is encrypted using the receiver's public key 322 and sent to the recipient.

Once the message is received, the recipient begins by decrypting the signature with the recipient's private key. Then, the validity of $ID_1$ 308 will be checked against known servers ID, and if correct, the content of the message 320 may be read. Then, the sender's private key is used to decrypt the remainder of the signature. Once readable, the validity of the sender's ID and the and the purpose for the message are checked. As a final check, the time mark is used to show whether the signature has been used.

The use of a digital signature as described uses asymmetric cryptography to ensure the security of the message by requiring that the data encrypted by a first key must be decrypted with a second key. Furthermore, as the signature is encrypted by recipient's public key, only the receiver can decrypt it and read the related information contained therein. Similarly, only the sender can sign the signature if it can be decrypted with sender's private key. Moreover, the time mark shows how many times the sender has signed the signature when communicating to the recipient. Accordingly, with each use of the signature, the time mark is incremented by one, which guarantees that each signature is unique and prevents the signature from being reused.

A further feature of the signature system is the requirement for the sender to know $ID_1$ and $ID_2$. This information is provided to all the servers by the coordinator. Furthermore, the signature includes two encryption processes, which would represent a cost in time. A further cost in time is provided by the recipient needing to determine the sender from $ID_1$. This time cost increases the difficulty of breaching the system and reduces the likelihood of a network random attack.

Pre-Process

Figure 4:
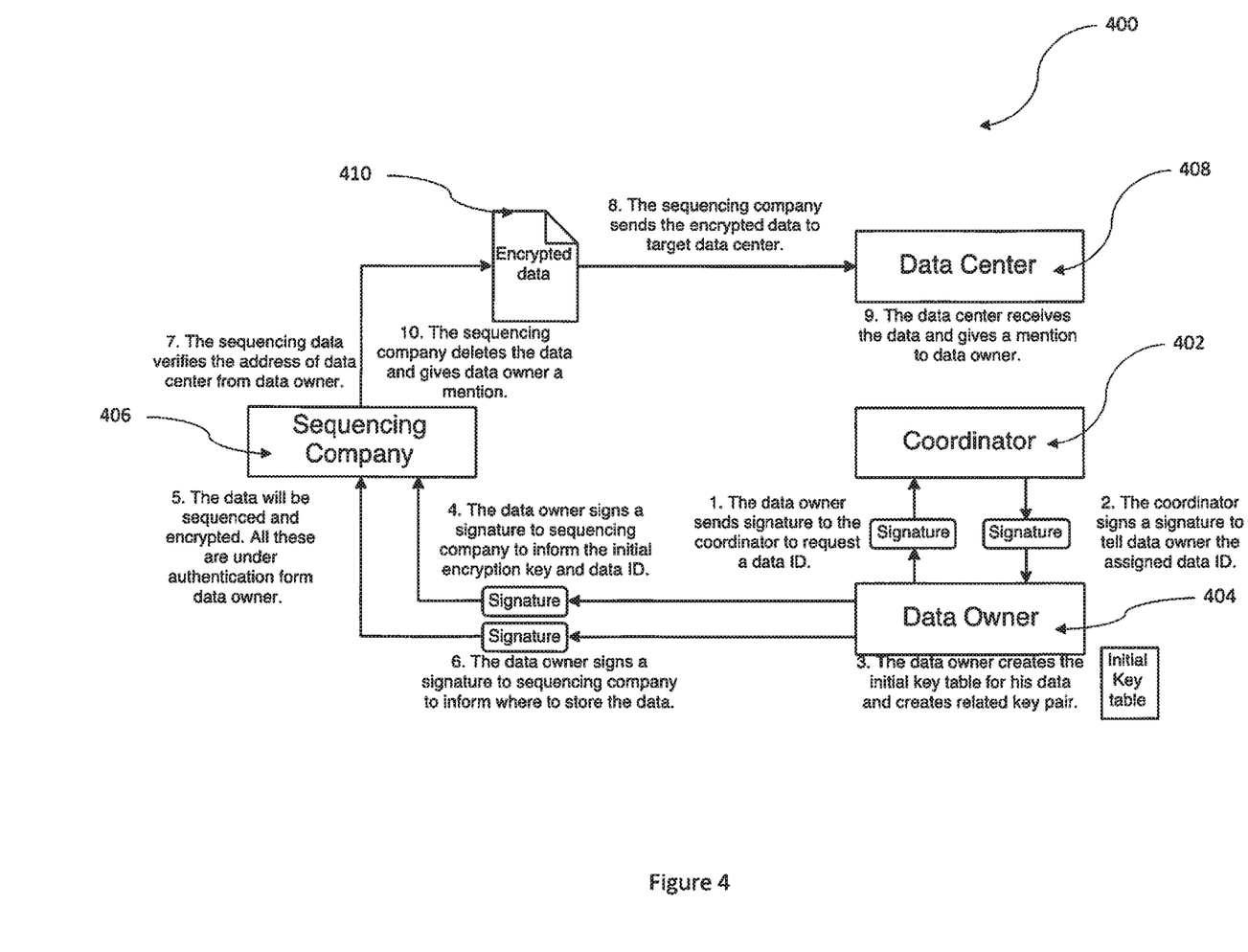
FIG. 4 shows an embodiment of the present invention.

The five sub-operations are now described in further detail. In an embodiment, the present invention includes the pre-process sub-procedure and data storage sub-procedure. Referring to FIG. 4, the processes 400 of pre-process and data storage sub-procedures are described in further detail.

Before joining the system 400, a server must first send a request to the coordinator 402. The coordinator 402 performs one or more tests to ensure the server requiring access to the system is legitimate and is not a potential attacker. Once the coordinator 402 has verified the server, the coordinator 402 installs the computer system of the present invention as a program on the server and any other server who wishes to join the system.

Once the program has been installed and initialised, the data owner server 404 sends a message to the coordinator requesting that they be provided with a data ID corresponding to the genetic data that is to be sequenced by the genetic sequencing server 406. The coordinator 402 checks the validity of the request and provides this information to the data owner server 404 within a message verified by a digital signature. Each message, between any of the servers, includes a signature created by the sender of the message, which includes the content of the message and has been created in the manner described above. The program on each server produces a cryptographic initial key table and the related pair of asynchronous cryptographic keys. Each server sends the public key to the coordinator 402. For example, in FIG. 4, the server who generates the initial key table and key pair is the data owner server 404.

The coordinator 402 adds the server's public key into the public key table, which is published to all servers. Then, based on the published table, each server may produce a communication table to record all communication with each of the other servers. The communication table is used to create the time mark for the signature of each server. As the key tables are constantly changed, the coordinator 402 is required to periodically publicise the public key table as it is updated. Using the updated public key information, each server updates their local public key table, and accordingly modifies the communication table. The updating of the public information by the coordinator 402 ensures that each of the servers is kept updated on the changes to the public keys to facilitate continued operation of the computer system in an efficient and effective manner.

Data Storage

Continuing to refer to FIG. 4, the data owner server 404 sends a message and signature to the genetic data sequencing server 406 to sequence their genetic data and transmit the data to a secure data centre 406 for storage. The genetic data sequencing server may also be referred to as the genetic data sequencing server. The data owner server 404 sends the initial encryption key and data ID. After receiving the signature, the sequencing server 406 verifies related information for data owner server 404 online. Then, the genetic data associated with the data is sequenced and encrypted using the initial encryption key. The data owner server 402 is notified when the process finishes. In an embodiment, the program installed one the genetic sequencing server is embedded within the function of the genetic sequencing process which encrypts the raw genetic data simultaneously as the genetic data is sequenced, which ensures the sequencing server 406 cannot duplicate the un-encrypted genetic data.

Following the encryption of the genetic data, the data owner server 404 provides a signature to genetic sequencer server 406 to inform them of which data centre server 408 is to store the encrypted data 410. The genetic sequencer server 406 verifies the data owner server's instructions with the data centre server 408. The genetic sequencer server 406 transmits the encrypted data to the authorised data centre server 408. When data centre server 408 receives the data, the data centre server 408 checks whether the received data is the target encrypted data 410 and reports the receipt of the data to the data owner server 404. Finally, the genetic sequencer server 406 deletes the data.

Data Movement

Figure 5:
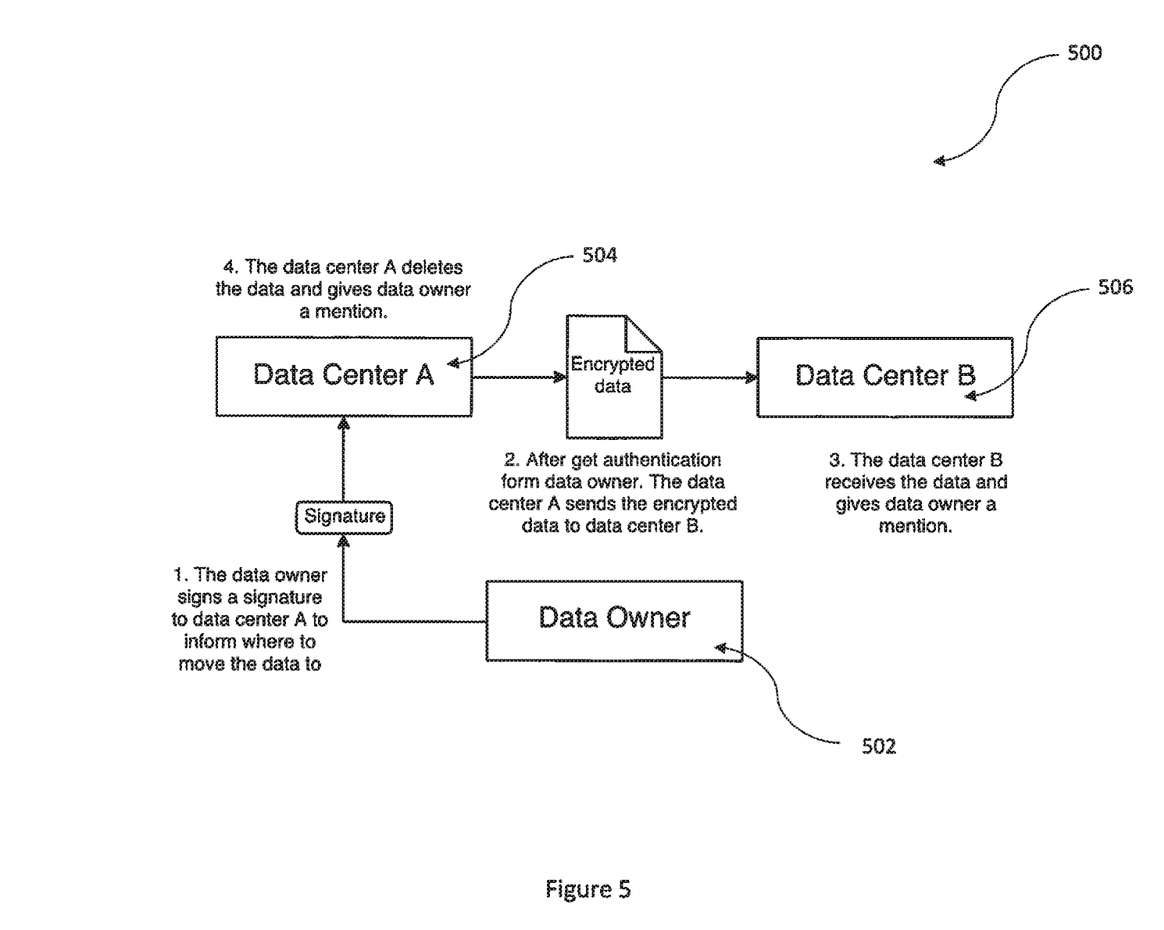
FIG. 5 shows a further embodiment of the present invention.

In an embodiment, the encrypted genetic data of the data owner server can be transmitted between data centres. Referring to FIG. 5, the process 500 of transferring the encrypted data from one data centre to another is shown in detail.

The following example is merely an example to illustrate the workings of the invention. Accordingly, the skilled addressee would understand that no gloss or limitations should be imposed on the present invention according to the example. In the example, the data owner server 502 wishes to transfer their encrypted genetic data stored at data centre A 504 to data centre B 506. This may occur due to a number of reasons, which may include ease of access to the information, the closing or moving of data centres, the cost of data storage, or mere personal preference.

Firstly, the data owner server 502 sends a signature to data centre A 504 to clarify the data that is to be transmitted and where the data is to be transmitted. After receiving and decrypting the signature and related message, the data centre A 504 confirms that the data relates to the data owner, then transmits the encrypted data to data centre B 506. Data centre B receives the data and checks related information, and once the validity of the transmission is confirmed, the data centre B 506 informs the data owner server 502. Furthermore, upon successful transmission, data centre B 506 also asks data centre A 504 to delete the encrypted files.

Data Re-Encryption

During the process of transmitting the genetic information from one data centre to another, the data may be vulnerable to breach or may be viewable to the data centre. Accordingly, an embodiment of the invention includes a data re-encryption process which is shown in further detail in FIG. 6.

Figure 6:
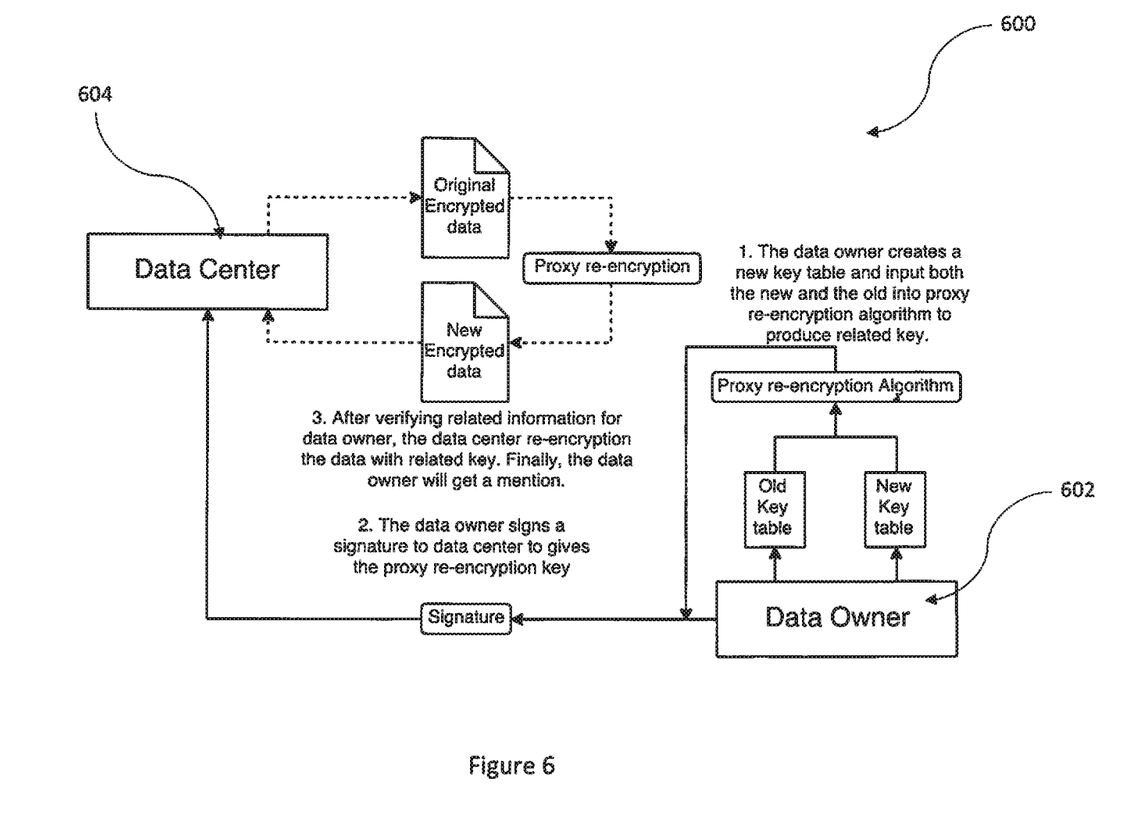
FIG. 6 shows an embodiment of the present invention.

The re-encryption process requires the data owner server 602 to generate a new key table, including the old key table which has been hashed using a Secure Hash Algorithm, and calculate a new asymmetric cryptographic key pair. Both of the old key pair and new key pair are run through a proxy re-encryption algorithm to generate the new encryption key. A proxy re-encryption algorithm is a cryptosystem that allow third parties (proxies) to alter encrypted data which has been encrypted for one server, so that it may be decrypted by another server. Proxy re-encryption schemes are very similar to asymmetric encryptions schemes but with two additional features, being the delegation of a direction and whether the re-encryption can be repeated. Each re-encryption is to be a unique combination of the previous cryptographic keys and is not be reversible between servers, the person skilled in the art would understand that the proxy re-encryption scheme should utilize algorithms which are non-transitive and uni-directional, that is, non-reversible and non-repeatable.

The data owner server 602 signs a signature to data centre 604 to provide the proxy re-encryption key. Having received the signature, the data centre verifies the signature online and the encrypted data will be re-encrypted through a proxy re-encryption algorithm.

Data Process

Genetic data is used to investigate the genetic makeup of a specific person or their relatives. A genetic service provider undertakes the analysis of the genetic data and provides the results of the genetic analysis to the data owner server. The analysis may be undertaken for a number of reasons such as investigating the presence of genetic or inherited disorders, diagnosis of certain diseases such as cancer, and the detection of mutations, fusion genes, and DNA copy number changes. In order for the genetic data analysing server to undertake the analysis, the server must be provided with a copy of the genetic data.

Figure 7:
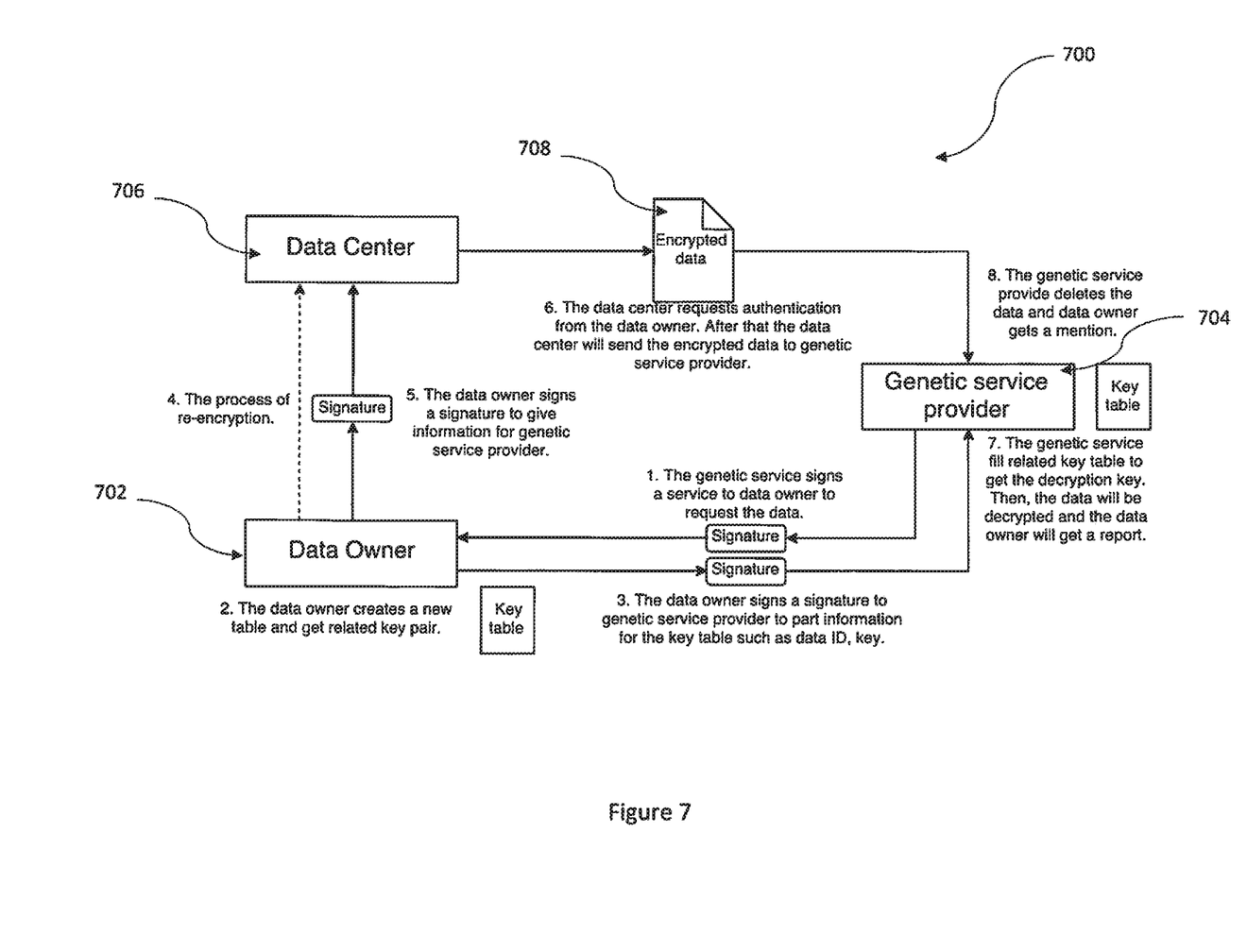
FIG. 7 shows a further embodiment of the present invention.

FIG. 7 shows the process for transmitting the data owner server's genetic data from the data centre to the genetic data analysing server 700. Prior to analysis of the genetic data, the data owner server 702 must select and accept the analysis service provided by genetic data analysing server 704. The data owner server 702 instructs the data centre server 706 to send the encrypted data 708 to the genetic data analysing server 704 and guide the genetic data analysing server to use the data. As mentioned above, the genetic data has been re-encrypted to enable secure transmission by the data centre 706. After the re-encryption process, the data owner server 702 provides a signature to the data centre 706 to verify the recipient genetic data analysing server, after which the data centre 706 sends the re-encrypted data to the genetic data analysing server 704.

Prior to, or during the transmission of the re-encrypted data 708, the genetic data analysing server 704 provides a signature to the data owner server 702 which includes a request to use the data owner server's 702 genetic data. Once the data owner server 702 has received the signature, the data owner server 702 provides a signature to the genetic data analysing server 704 which includes the data ID, table key, time block and previous table hash result. That is, the data owner server 702 provides the genetic data analysing server 704 with all the information necessary to decrypt the re-encrypted data 708. With the information provided by the data owner server 702, the genetic data analysing server 704 completes the key table within the limited time block to obtain the related decryption key. Once in possession of the decryption key, the genetic data analysing server 704 uses the decryption key to decrypt the data. The genetic data analysing server 704 can read and use the raw data as collected by the sequencing server (not shown). Once the decryption has been performed, the genetic data analysing server 704 sends a report related to the decryption to data owner server 702.

Now the data has been decrypted, the genetic data analysing server uses the data to conduct their analysis. Once the data is no longer required, the genetic data analysing server manually deletes the data, or the program installed on the genetic data analysing server 704 automatically deletes the data after each use to ensure that none of the genetic data can be reused.

Advantages

The heart of a secure system is its cryptographic mechanism. In the present invention, only the data owner server and authorised servers can access decryption key for one encrypted data. It is assumed that there are two main types of attackers that would be likely to attempt to breach the system described above. The first one is a network hacker, who does not register within the system. Another one is an authorized server attempting to decrypt the data owner server's data.

The detailed design ensures the security of genetic data in several aspects. Firstly, the system is structured to securely control the data in respect to each use. For example, the coordinator update and maintain the system, they have no control over or access to the data. As such, only the data owner server maintains that privilege. This is also seen in the use of the proxy the re-encryption system, where the data centre only performs the re-encryption on already encrypted genetic data and the genetic data analysing server is not able to reuse the data. This means that the raw data is not available to the data centre and the security risk is lowered. Finally, several settings are made for decryption data, so the genetic data analysing serveries not able to reuse the data. As such, the operations for genetic data such as data movement, encryption and decryption are provided in a peer to peer (P2P) network model. The use of the P2P structure enables the decentralization of the system and enables message transmission to be simplified and discrete, whilst also enhancing the security of the data.

Secondly, the most private information such as table key and the data owner server's private key are generated locally and are only accessible to the data owner server, which decreases the possibility of information leakage.

Thirdly, any access to genetic data can only be performed under the authentication of the data owner server. Furthermore, data the owner can track the related processing records through the chain of linked hashed cryptography tables.

Fourthly, each operation for genetic data is double-authorized by the data owner server through both providing a signature and online verification. This provides additional security to protect against a breach as any hacker or unauthorised server would need to account for both security methods in order to access the data.

Furthermore, the security of cryptography key table can be mathematically demonstrated. Assume the number of data records for the whole system is a and the number of servers is b. Each time block lasts t days. The lengths for data ID, server ID, encrypted time stamp is $l_{id1}$, $l_{id2}$ and $l_{id3}$, respectively. The sizes for key part and hash result are $l_{Key}$ and $l_{Hash}$. The unit used here is a byte. As mentioned before, the attackers can be divided into two main groups; a network hacker and an authorized server. It may be assumed that the attackers may have already acquired part of the targeted data. Therefore, there may be different situations with a range of difficulty of attempting to break the encryption. Computational complexities to crack the decryption key under different prior knowledge are shown in table 3.

TABLE 3

Time complexity for various attackers

| Group | Attacker | Time Complexity |
|---|---|---|
| Network Hacker | With system ID tables | $O(ab2^{8l_{id3}+8l_{key}+8l_{hash}})$ |
|  | Without any prior information | $O(2^{8l_{id1}+8l_{id2}+8l_{id3}+8l_{key}+8l_{hash}})$ |
| Unauthorized Server | Having none information for the data | $O(ab2^{8l_{key}+8l_{hash}})$ |
|  | Last server for the data | $O(ab2^{8l_{key}})$ |

As shown in table 3, the lowest time complexity to break in the system for unauthorized server is $O(ab2^{8l_{key}})$. However, since the time stamp will change after t days, the unauthorized server would be required to obtain the decryption key within a time block. Assume the computing power is C HZ and the verification requires k computations. To avert the attack from unauthorized server, the below equation should be satisfied.

$$abk2^{8l_{key}} \gg 86400tC$$

Since a, b, k and t are relatively fixed compared to $l_{key}$ and C, the above equation can be approximated as $l_{key} \gg \lg C$. The key for cryptography table does not require to be readable and memorable, so we can increase the size within memory limit. Therefore, the above equation can be easily satisfied.

Assume the probability that the after t time the attacker will get correct decryption key is P.

$$P = 1 - \left(1 - \frac{1}{abk2^{8l_{key}}}\right)^{86400tC}$$

We simplify the equation by assuming the computational power provided by attacker is W. The total computation required is $\lambda$ times W. Since W is large and keeps increasing, we can assume that W is heading towards infinity. Then, the equation can be simplified.

$$P \approx \lim_{W \to \infty} 1 - \left(1 - \frac{1}{\lambda W}\right)^W$$

$$P \approx 1 - \frac{1^{\frac{1}{\lambda}}}{e}$$

The relationship between P of $\lambda$ is shown in table 4. From the table, when the $\lambda$ is large enough, the relationship between $\lambda$ and P is nearly linear. We can almost ensure the unauthorized server cannot guess the correct key when $\lambda$ is a large number such as 1000.

TABLE 4

Relationship between the attacked probability and $\lambda$

| $\lambda$ | P |
|---|---|
| 0.1 | 0.99995 |
| 1 | 0.63212 |
| 10 | 0.09516 |
| $10^1$ | $9.95017 \times 10^{-3}$ |
| $10^2$ | $9.99950 \times 10^{-4}$ |
| $10^3$ | $9.99950 \times 10^{-5}$ |

For network hacker, the lowest required time complexity is $O(ab2^{8l_{id3}+8l_{key}+8l_{hash}})$. A comparison with the unauthorized server can be made. The least computation needed for hacker is $O(2^{8l_{id3}+8l_{hash}})$ times the least computational cost for unauthorized server. However, there is a time limit for unauthorized server t, since he can only inquire the correct time stamp from the coordinator within the specific time block. However, that limit does not exist for network hacker. Assume a lifespan for a data is u years. We assume the requirement that the table will not be cracked by unauthorized server are satisfied. To ensure the table will not cracked by hackers, the below equation should be satisfied.

$$2^{8l_{id3}+8l_{hash}} \gg 365 \times \frac{u}{l}$$

Since the length for the Secure Hash Algorithm output or digest is at least 160 bytes, the equation above can be satisfied.

Disclaimers

Throughout this specification, unless the context requires otherwise, the word "comprise" or variations such as "comprises" or "comprising", will be understood to imply the inclusion of a stated integer or group of integers but not the exclusion of any other integer or group of integers.

Those skilled in the art will appreciate that the invention described herein is susceptible to variations and modifications other than those specifically described. The invention includes all such variation and modifications. The invention also includes all of the steps, features, and formulations referred to or indicated to in the specification, individually or collectively and any and all combinations or any two or more of the steps or features.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

In the above description, reference is made to "breaches", "attackers" and "hackers". It will be understood that the aforementioned terms are used to provide the reader with colloquial labels that aim to provide a clear and understandable example of the embodiment or embodiments of the present invention. It will be understood, that the terms are provided solely for illustrative purposes and the reader is not to draw any gloss from the aforementioned terms. As such, the aforementioned terms used should not be used to limit or otherwise vary the scope of the embodiments or the broader invention described and defined herein.

It will also be appreciated that where methods and systems of the present invention and/or embodiments are implemented by computing systems or partly implemented by computing systems then any appropriate computing system architecture may be utilised. This includes standalone computers, network computers and dedicated computing devices (such as field-programmable gate arrays).

Where the terms "computer", "computing system" and "computing device" are used in the specification, these terms are intended to cover any appropriate arrangement of computer hardware for implementing the inventive concept and/or embodiments described herein.

The invention claimed is:

1. A computer system for secure storage, transmission, and access of genetic data comprising:
   a coordinator server arranged to communicate with a data owner server, a genetic data generating server, a genetic data analysing server, and a genetic data storage server, wherein the coordinator server includes a memory storing a coordinator program arranged to
      update secure access information to facilitate communication among the data owner server, the genetic data storage server, the genetic data generating server, and the genetic data analysing server, the secure access information including (i) public keys of asymmetric cryptographic key pairs generated by each of the data owner server, the genetic data storage server, the genetic data generating server, and the genetic data analysing server, and (ii) time stamps comprising encrypted time blocks, and
      assign unique identification number to each of the data owner server, the genetic data generating server, the genetic data analysing server, and the genetic data storage server, and to genetic data of the data owner;
   wherein the coordinator server is arranged to communicate the secure access information in a manner that allows the genetic data storage server to act as a proxy server between the genetic data generating server and the genetic data analysing server,
   wherein the coordinator server does not store, transmit, and access genetic data,
   wherein the coordinator server is arranged to provide the unique identification numbers and the time stamps to facilitate completion of a cryptographic key table, the cryptographic key table includes unique identification number of the genetic data, unique identification number of the data owner server, unique identification number of the genetic data analysing server, a time stamp specifying the time block during which the genetic data analysing server is allowed to decrypt encrypted genetic data provided by the genetic data storage server to the genetic data analysing server, a key for the cryptographic key table, and a hash result of a previous cryptographic key table, and
   wherein content of the cryptographic key table is arranged to be run through a secure hash algorithm to produce a decryption key for decrypting the encrypted genetic data so that the genetic data analysing server can analyse the genetic data, and the genetic data analysing server has to complete the cryptographic key table within the time block to obtain the decryption key.

2. The computer system in accordance with claim 1, wherein the genetic data generating server encrypts the genetic data using an encryption key created by the data owner server and transmits the encrypted data to the genetic data storage server.

3. The computer system in accordance with claim 2, wherein the genetic data storage server is instructed to re-encrypt the encrypted data using a re-encryption key created by the data owner server to produce the encrypted genetic data.

4. The computer system in accordance with claim 3, further comprising the genetic data storage server and the genetic data analysing server, wherein the genetic data storage server is arranged to transmit the encrypted genetic data to the genetic data analysing server.

5. The computer system in accordance with claim 1, wherein the coordinator program is arranged to instruct the genetic data analysing server to delete the genetic data after the genetic data is analysed.

6. The computer system of claim 1, further comprising the data owner server, wherein the data owner server is arranged to communicate with the coordinator server, the genetic data storage server, the genetic data generating server, and the genetic data analysing server through the exchange of one or more digital signatures.

7. The computer system of claim 6, wherein each of the one or more digital signatures is generated by:
   encrypting a public key for a sender and a public key for a receiver using a secure hash algorithm;
   transferring the hashed publish keys into identifiers;
   adding a version identifier and a time mark to the identifiers to create a signature content;
   encrypting the signature content using a private key of the sender;
   combining the encrypted signature content with an identifier of the sender and a message to the communicated to the receiver; and
   encrypting the entire signature and message using the public key of the receiver.

8. A computing network for the secure storage, transmission, and access of genetic data comprising:
   a coordinator server in communication with a data owner server and a genetic data generating server, the genetic data generating server is in communication with a genetic data storage server and the genetic data storage server is in communication with a genetic data analysing server, the coordinator server including a memory storing a coordinator program arranged to
      update secure access information to facilitate communication among the data owner server, the genetic data storage server, the genetic data generating server, and the genetic data analysing server, the secure access information including (i) public keys of asymmetric cryptographic key pairs generated by each of the data owner server, the genetic data storage server, the genetic data generating server, and the genetic data analysing server, and (ii) time stamps comprising encrypted time blocks, and
      assign unique identification number to each of the data owner server, the genetic data generating server, the genetic data analysing server, and the genetic data storage server and to genetic data of the data owner,
   wherein the genetic data of a data owner is encrypted by the genetic data generating server and decrypted by the genetic data analysing server,
   wherein the coordinator server does not store, transmit, and access genetic data,
   wherein the coordinator server is arranged to provide the unique identification numbers and the time stamps to facilitate completion of a cryptographic key table, the cryptographic key table includes unique identification number of the genetic data, unique identification number of the data owner server, unique identification number of the genetic data analysing server, a time stamp specifying the time block during which the genetic data analysing server is allowed to decrypt encrypted genetic data provided by the genetic data storage server to the genetic data analysing server, a key for the cryptographic key table, and a hash result of a previous cryptographic key table, and wherein content of the cryptographic key table is arranged to be run through a secure hash algorithm to produce a decryption key for decrypting the encrypted genetic data so that the genetic data analysing server can analyse the genetic data, and the genetic data analysing server has to complete the cryptographic key table within the time block to obtain the decryption key.

9. The computing network in accordance with claim 8, further comprising the data owner server, wherein the data owner server is arranged to generate a decryption key using a cryptographic operation.

10. The computing network in accordance with claim 9, wherein the cryptographic operation includes a series of one or more previous cryptographic operations.

11. The computing network in accordance with claim 10, wherein the series of one or more previous cryptographic operations are encrypted by a hash function.

12. The computing network in accordance with claim 9, wherein the decryption key is used to generate an encryption key through elliptic curve cryptography.

13. The computing network in accordance with claim 12, further comprising the genetic data generating server, wherein the genetic data generating server is arranged to encrypt the genetic data using the encryption key created by the data owner server and to transmit-a the encrypted data to the genetic data storage server.

14. The computing network in accordance with claim 8, further comprising the genetic data storage server, wherein the genetic data storage server is instructed to re-encrypt the encrypted genetic data using a re-encryption key created by the data owner server.

15. The computing network in accordance with claim 14, wherein the genetic data storage server is arranged to transmit the re-encrypted data to the genetic data analysing server.

16. The computing network in accordance with claim 8, wherein the coordinator program is arranged to instruct the genetic data analysing server to delete the genetic data after the genetic data is analysed.

17. The computer system of claim 8, further comprising the data owner server, wherein the data owner server is arranged to communicate with the coordinator server, the genetic data storage server, the genetic data generating server, and the genetic data analysing server through the exchange of one or more digital signatures.

18. The computer system of claim 17, wherein each of the one or more digital signatures is generated by:
encrypting a public key for a sender and a public key for a receiver using a secure hash algorithm;
transferring the hashed publish keys into identifiers;
adding a version identifier and a time mark to the identifiers to create a signature content;
encrypting the signature content using a private key of the sender;
combining the encrypted signature content with an identifier of the sender and a message to the communicated to the receiver; and
encrypting the entire signature and message using the public key of the receiver.

19. A computer system for secure storage, transmission, and access of genetic data comprising:
a coordinator server in communication with a data owner server, a genetic data storage server, a genetic data generating server, and a genetic data analysing server, the coordinator server including a memory storing a coordinate program arranged to
update secure access data that facilitates communication among the data owner server, the genetic data storage server, the genetic data generating server, and the genetic data analysing server, the secure access information including (i) public keys of asymmetric cryptographic key pairs generated by each of the data owner server, the genetic data storage server, the genetic data generating server, and the genetic data analysing server, and (ii) time stamps comprising encrypted time blocks, and
assign unique identification number to each of the data owner server, the genetic data generating server, the genetic data analysing server, and the genetic data storage server and to genetic data of the data owner;
wherein the genetic data storage server stores the encrypted genetic data transmitted from the genetic data generating server and re-encrypts the encrypted data prior to transmission of the encrypted genetic data to the genetic data analysing server whereby the genetic data analysing server can only unencrypt the genetic data upon receipt of the secure access information from the coordinator server,
wherein the coordinator server does not store, transmit, and access genetic data,
wherein the coordinator server is arranged to provide the unique identification numbers and the time stamps to facilitate completion of a cryptographic key table, the cryptographic key table includes unique identification number of the genetic data, unique identification number of the data owner server, unique identification number of the genetic data analysing server, a time stamp specifying the time block during which the genetic data analysing server is allowed to decrypt encrypted genetic data provided by the genetic data storage server to the genetic data analysing server, a key for the cryptographic key table, and a hash result of a previous cryptographic key table, and
wherein content of the cryptographic key table is arranged to be run through a secure hash algorithm to produce a decryption key for decrypting the encrypted genetic data so that the genetic data analysing server can analyse the genetic data, and the genetic data analysing server has to complete the cryptographic key table within the time block to obtain the decryption key.

20. The computer system in accordance with claim 19, further comprising the data owner server, wherein the data owner server is arranged to generate a decryption key using a cryptographic operation.

21. The computer system in accordance with claim 20, wherein the cryptographic operation includes a series of one or more previous cryptographic operations.

22. The computer system in accordance with claim 21, wherein the series of one or more previous cryptographic operations are encrypted by a hash function.

23. The computer system in accordance with claim 20, wherein the decryption key is used to generate an encryption key through elliptic curve cryptography.

24. The computer system of claim 19, further comprising the data owner server, wherein the data owner server is arranged to communicate with the coordinator server, the genetic data storage server, the genetic data generating server, and the genetic data analysing server through the exchange of one or more digital signatures.

25. The computer system of claim 24, wherein each of the one or more digital signatures is generated by:

encrypting a public key for a sender and a public key for a receiver using a secure hash algorithm;

transferring the hashed publish keys into identifiers;

adding a version identifier and a time mark to the identifiers to create a signature content;

encrypting the signature content using a private key of the sender;

combining the encrypted signature content with an identifier of the sender and a message to the communicated to the receiver; and encrypting the entire signature and message using the public key of the receiver.

26. A computer system for the secure storage, transmission, and access of genetic data comprising:

a data owner server, a genetic data storage server, a genetic data generating server, a genetic data analysing server, and a coordinator server in communication with the data owner server, the genetic data storage server, the genetic data generating server, and the genetic data analysing server, wherein the coordinator server includes a memory storing a coordinator program arranged to update secure access information to facilitate communication among the data owner server, the genetic data storage server, the genetic data generating server, and the genetic data analysing server, the secure access information including (i) public keys of asymmetric cryptographic key pairs generated by each of the data owner server, the genetic data storage server, the genetic data generating server, and the genetic data analysing server, and (ii) time stamps comprising encrypted time blocks, and assign unique identification number to each of the data owner server, the genetic data generating server, the genetic data analysing server, and the genetic data storage server and to genetic data of the data owner;

wherein the coordinator server is arranged to operate as a proxy server in a decentralised data sharing network by verifying the identity each of the genetic data storage server, the genetic data generating server, and the genetic data analysing server and facilitate the secure transmission and storage of the genetic data by updating the public keys generated by the data owner server, the genetic data storage server, the genetic data generating server, and the genetic data analysing server, wherein the coordinator server does not store, transmit, and access genetic data, wherein the coordinator server is arranged to provide the unique identification numbers and the time stamps to facilitate completion of a cryptographic key table, the cryptographic key table includes unique identification number of the genetic data, unique identification number of the data owner server, unique identification number of the genetic data analysing server, a time stamp specifying the time block during which the genetic data analysing server is allowed to decrypt encrypted genetic data provided by the genetic data storage server to the genetic data analysing server, a key for the cryptographic key table, and a hash result of a previous cryptographic key table, and wherein content of the cryptographic key table is arranged to be run through a secure hash algorithm to produce a decryption key for decrypting the encrypted genetic data so that the genetic data analysing server can analyse the genetic data, and the genetic data analysing server has to complete the cryptographic key table within the time block to obtain the decryption key.

27. The computer system in accordance with claim 26, wherein the coordinator server is arranged to verify the identities of the data owner server, the genetic data storage server, the genetic data generating server, and the genetic data analysing server.

28. The computer system in accordance with claim 26, wherein the data owner server is arranged to generate a decryption key using a cryptographic operation.

29. The computer system in accordance with claim 28, wherein the cryptographic operation includes a series of one or more previous cryptographic operations.

30. The computer system in accordance with claim 29, wherein the series of one or more previous cryptographic operations are encrypted by a hash function.

31. The computer system in accordance with claim 28, wherein the decryption key is used to generate an encryption key through elliptic curve cryptography.

32. The computer system in accordance with claim 26, wherein the genetic data generating server is instructed to encrypt the genetic data using an encryption key created by the data owner server and to transmit the encrypted data to the genetic data storage server.

33. The computer system in accordance with claim 32, wherein the coordinator program instructs the genetic data generating server to delete the genetic data after the genetic data is generated.

34. The computer system in accordance with claim 32, wherein the genetic data storage server is instructed to re-encrypt the encrypted data using a re-encryption key created by the data owner server to produce the encrypted genetic data.

35. The computer system in accordance with claim 34, wherein the genetic data storage server is arranged to transmit the encrypted genetic data to the genetic data analysing server.

36. The computer system in accordance with claim 26, wherein the coordinator program is arranged to instruct the genetic data analysing server to delete the genetic data after the genetic data is analysed.

37. The computer system in accordance with claim 26, wherein the genetic data storage server comprises of two or more genetic data storage servers.

38. The computer system in accordance with claim 37, wherein the genetic data storage server is instructed to re-encrypt the encrypted data using a re-encryption key created by the data owner server to produce re-encrypted genetic data.

39. The computer system in accordance with claim 38, wherein the first data storage server transmitting the re-encrypted genetic data to a second genetic data storage server designated by the data owner server.

40. The computer system in accordance with claim 39, wherein the coordinator program instructs the first genetic data storage server to delete the encrypted data after the second genetic data storage server has received the re-encrypted genetic data.

41. The computer system of claim 26, wherein the data owner server is arranged to communicate with the coordinator server, the genetic data storage server, the genetic data generating server, and the genetic data analysing server through the exchange of one or more digital signatures, and wherein each of the one or more digital signatures is generated by:

encrypting a public key for a sender and a public key for a receiver using a secure hash algorithm;
transferring the hashed publish keys into identifiers;
adding a version identifier and a time mark to the identifiers to create a signature content;
encrypting the signature content using a private key of the sender;
combining the encrypted signature content with an identifier of the sender and a message to the communicated to the receiver; and
encrypting the entire signature and message using the public key of the receiver.

* * * * *